United States Patent
Tanaka

(10) Patent No.: US 7,828,736 B2
(45) Date of Patent: Nov. 9, 2010

(54) ELECTRONIC SCAN TYPE ULTRASOUND DIAGNOSTIC INSTRUMENT

(75) Inventor: Toshizumi Tanaka, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1690 days.

(21) Appl. No.: 11/041,295

(22) Filed: Jan. 25, 2005

(65) Prior Publication Data
US 2005/0165314 A1    Jul. 28, 2005

(30) Foreign Application Priority Data
Jan. 27, 2004    (JP)    .............................. 2004-017849
Mar. 31, 2004    (JP)    .............................. 2004-102391

(51) Int. Cl.
*A61B 8/14*    (2006.01)
*H02N 2/00*    (2006.01)
(52) U.S. Cl. ...................................... 600/459; 310/335
(58) Field of Classification Search ................. 600/459; 310/335
See application file for complete search history.

(56) References Cited

U.S. PATENT DOCUMENTS

| | | | | |
|---|---|---|---|---|
| 4,448,075 A | * | 5/1984 | Takemura et al. | 73/626 |
| 5,081,993 A | * | 1/1992 | Kitney et al. | 600/455 |
| 5,327,895 A | * | 7/1994 | Hashimoto et al. | 600/459 |
| 5,349,960 A | * | 9/1994 | Gondo | 600/455 |
| 5,401,913 A | * | 3/1995 | Gerber et al. | 174/264 |
| 5,443,070 A | | 8/1995 | Mniece | |
| 6,171,248 B1 | * | 1/2001 | Hossack et al. | 600/459 |
| 6,873,868 B2 | * | 3/2005 | Furnish | 600/435 |

FOREIGN PATENT DOCUMENTS

JP    09291269 A    * 11/1997

* cited by examiner

*Primary Examiner*—Eric F Winakur
*Assistant Examiner*—Helene Bor
(74) *Attorney, Agent, or Firm*—Oblon, Spivak, McClelland, Maier & Neustadt, L.L.P.

(57) ABSTRACT

An electronic scan type ultrasound diagnostic instrument employing an ultrasound transducer which is constituted by an array of transducer elements in a predetermined direction and adapted to drive a plural number of adjacent located transducer elements in simultaneous or delayed action mode. Arrayed transducer elements are divided into a plural number of transducer assembly units in the arrayed direction. Each one of the transducer elements is provided with a separate electrode which is connected with a signal line separately from other transducer elements, and a common electrode which is connected commonly with one or a plural number of transducer elements. A signal line from a separate electrode of a transducer element is short circuited with a signal line from a transducer element in a different transducer assembly unit and connected together to a single wiring cable.

9 Claims, 10 Drawing Sheets

ELECTRONIC SCAN TYPE ULTRASOUND DIAGNOSTIC INSTRUMENT

BACKGROUND OF THE INVENTION

1. Field of the Art

This invention relates to an ultrasound diagnostic instrument to be used in medical fields for examination of internal body tissues, and more particularly to an electronic scan type ultrasound diagnostic instrument incorporating an array of a large number of ultrasound transducer elements to be sequentially driven for simultaneous or delayed transmit/receive actions.

2. Prior Art

Ultrasound diagnostic devices have been in use in medical fields for examination of internal body tissues of patients. Ultrasound diagnostic devices are arranged as a device for acquiring topographic ultrasound images of internal body tissues by processing echo signals of ultrasound pules which have been transmitted from ultrasound transducer elements toward an internal body portion of particular interest. Ultrasound transducer elements are arranged to make a scan over a predetermined range, either in a mechanical scan or in an electronic scan.

In the case of an electronic scan type ultrasound diagnostic device, for example, an ultrasound transducer is constituted by a large number of transducer elements which are arranged in a linear shape, arcuate shape or cylindrical shape or in a planar-array matrix. An ultrasound scan is made by locating the ultrasound transducer at a predetermined position and sequentially driving the ultrasound transducer elements one after another. In some cases, for transmitting ultrasound pulses in a certain beam diameter or for focusing ultrasound pulses to a certain depth, ultrasound pulses are transmitted from a plural number of transducer elements simultaneously or with predetermined time lags.

In this connection, in the case of an ultrasound transducer which is constituted by a large number of transducer elements as mentioned above, there has been a problem, in addition to complication in construction, in that it is inevitable to provide a cable of a large diameter containing a bundle of a large number of hard-wires for making wring connections to and from the respective transducer elements. Let alone transmission of ultrasound pules from outside a patient's body, the use of a thick cable is undesirable for an ultrasound probe having an ultrasound transducer at the fore end of an insert portion to be introduced into a body cavity of a patient, because the thick cable will not only degrade maneuverability of the probe at the time of insertion into a patient's body but cause greater pains on the part of the patient.

Regarding a wiring system for a large number of arrayed transducer elements, attempts have been made to reduce the number of wires by dividing transducer elements in an array into groups except those transducer elements which are driven simultaneously or with predetermined time delays (hereinafter referred to as "transducer elements interrelated for simultaneous or delayed actions"), and using common wires to the transducer groups, for example, as disclosed in Japanese Laid-Open Patent Application 2003-319938. Namely, according to this prior art, wiring connections are made to a large number of arrayed transducer elements by the use of switching elements. Signal lines to the transducer elements in an array are short circuited at every six or sixteen transducer elements.

The above-mentioned prior art wiring system succeeded in reducing the number of wires, but still has a problem that the use of switching elements for the respective signal lines results in an ultrasound transducer which is more complicated in construction and larger in size. Therefore, if the ultrasound transducer is incorporated into an insertion type ultrasound diagnostic instrument, a fore end portion of an insertion tube will become too bulky in consideration of maneuverability of the instrument at the time of insertion into a body cavity.

SUMMARY OF THE INVENTION

In view of the foregoing situations, it is an object of the present invention to provide an electronic scan type ultrasound diagnostic instrument with a wiring system using a drastically reduced number of wires to and from transducer elements of an ultrasound transducer, permitting to reduce the diameter of a cable of signal lines.

It is another object of the present invention to provide an electronic scan type ultrasound diagnostic instrument having an insertion tube of a reduced diameter for insertion into a body cavity of a patient.

According to the present invention, in order to achieve the above-stated objectives, there is provided an electronic scan type ultrasound diagnostic instrument having an ultrasound transducer constituted by an array of transducer elements in a predetermined direction, and adapted to make an electronic scan by sequentially driving a plural number of adjacently located transducer elements into interrelated simultaneous or delayed actions, characterized in that: the transducer elements are divided into a plural number of transducer assembly units in the direction of the transducer array; each one of the transducer elements is provided with a separate electrode connected with an ultrasound signal transmit/reception line separately from other transducer elements and a common electrode connected with a common electrode of one or a plural number of other transducer elements; and a number of signal lines separately connected to separate electrodes of the respective transducer elements, each one of the signal line being short circuited with a signal line from a transducer element in a corresponding position in another transducer assembly unit and connected together to one same wiring cable.

With the arrangements just described, in the case of an ultrasound transducer which is composed of two transducer assembly units, the number of wiring cables can be reduced by half as compared with the total number of separate electrodes on the arrayed transducer elements. Accordingly, the case of an ultrasound transducer which is composed of three or four transducer assembly units, the number of wring cables can be reduced to ⅓ or ¼ of the total number of separate electrodes of the transducer elements. Namely, by holding a common electrode in one transducer assembly unit in ON state while holding a common electrode in another transducer assembly unit in OFF state, the arrayed transducer elements can be sequentially driven in interrelated simultaneous or delayed action mode. That is to say, the wiring system is adapted to drive a plural number of interrelated transducer elements in one transducer assembly unit alone, without driving other short circuited transducer elements in another transducer assembly unit.

In this instance, at the time of simultaneously driving a plural number of transducer elements which are located across a transitional portion between the preceding and succeeding transducer assembly units, it becomes necessary to turn ON common electrodes in both transducer assembly units. Therefore, transducer elements other than target transducer elements can be driven simultaneously. To avoid this, the ultrasound transducer is arranged to proceed to the transducer elements in the other transducer assembly unit, skipping drive of transducer elements in the transitional portion and interpolating ultrasound signals in the skipped transitional portion on the basis of preceding and succeeding ultrasound signals. Especially in a case where a couple of transducer elements are driven in a simultaneous or delayed action mode, fairly accurate ultrasound signals can be obtained by interpolation of only one signal line.

However, in a case where a greater number of transducer elements are driven in an interrelated simultaneous or delayed action mode, it becomes necessary to actually drive the transducer elements in the transitional portion between two transducer assembly units without skipping, for the purpose of obtaining more accurate ultrasound images while facilitating signal processing. For this purpose, common electrodes of transducer elements in each transducer assembly unit are divided into anterior and posterior group common electrodes each connected to one or a plural number of transducer elements, and an independent switching means is inserted in each one of wiring cables to the anterior and posterior group common electrodes in each transducer assembly unit. In this case, at the time of driving a plural number of transducer elements in a transitional portion between two transducer assembly units, a posterior group common electrode in a preceding transducer assembly unit and an anterior group common electrode in a succeeding transducer assembly unit are tuned on.

Wiring cables may be directly connected to electrodes of respective transducer elements. In this regard, it is desirable to connect wiring cables to transducer elements by the use of a flexible wiring board, for example, a filmy flexible wiring board. A filmy wiring board is wrapped around a backing material of an transducer array. The filmy wiring board is provided with electrodes in rows in its center portion and opposite side edge portions in relation with a wiring pattern which is formed on the front side of the film. In this instance, a wiring pattern can be formed on the rear side of the wiring film. Namely, the front side as well as the rear side of the filmy wiring board can be utilized as a surface area for forming a wiring pattern. In case electrodes are provided on the rear side of the filmy wiring board, a wiring pattern lines can be led out onto the front side at suitable points for connection to respective electrodes.

According to a more particular preferred form of the present invention, there is provided an electronic scan type ultrasound diagnostic instrument having an ultrasound transducer constituted by an array of transducer elements in a predetermined direction, and adapted to make an electronic scan by sequentially driving a plural number of adjacently located transducer elements into interrelated simultaneous or delayed actions, characterized in that: the transducer elements are divided into a plural number of transducer assembly units in the direction of the transducer array; each one of the transducer elements is provided with a separate electrode connected with an ultrasound signal transmit/reception line separately from other transducer elements and a common electrode connected with a common electrode of one or a plural number of other transducer elements; signal lines separately connected to separate electrodes of the respective transducer elements, each one of the signal line being short circuited with a signal line from a transducer element in a corresponding position in another transducer assembly unit and connected together to one and same wiring cable; the common electrodes being divided into an anterior group and a posterior group in each transducer assembly unit, the anterior group being common to transducer elements of a number equal to or larger than a number of transducer elements in preceding positions interrelated for simultaneous or delayed actions minus one; and wiring cables from anterior and posterior group common electrodes in each transducer unit being each connected with an independent switching means and thereby turned ON and OFF.

For example, in the case of an ultrasound transducer having thirty-two transducer elements in a linear array, driving three transducer elements simultaneously, first sixteen transducer elements in the array is grouped as a first transducer assembly unit, and the next sixteen transducer elements, that is to say, a transducer elements in a seventeenth position through to a transducer element in a thirty-second position are grouped as a second transducer assembly unit. Signal lines to separate electrodes of transducer elements in the first transducer assembly unit are each short circuited with a signal line to a separate electrode of a transducer elements in a corresponding position in the second transducer assembly unit by the use of a single wiring cable, more particularly, short circuiting signal lines of transducer No. 1 and transducer No. 17, transducer No. 2 and transducer No. 18, transducer No. 3 and transducer No. 19 and so forth. Accordingly, the number of wiring cables to be connected to the respective separate electrodes of the transducer elements can b reduced by half. On the other hand, with regard to common electrodes, the first two transducer elements in each transducer assembly unit are independently connected to an anterior group common electrode, while the remaining transducer elements in that assembly unit are connected to a posterior group common electrode. Wiring cables from the anterior and posterior group common electrodes are each turned on and off by an independent switching element. In this instance, there is no necessity for locating the switching elements in the vicinity of the transducer elements. Namely, the switching elements can be located on the side of a drive controller. At the time of driving transducer elements in the first transducer assembly unit, the switching elements of the anterior and posterior group common electrodes of the first assembly unit are turned ON, while other switching elements which are connected to the anterior and posterior group common electrodes of the second transducer assembly unit are turned OFF. At the time of simultaneously driving a last transducer element in the first transducer assembly unit and a first transducer element in the second transducer assembly unit, the anterior group common electrode of the first transducer assembly unit is turned OFF while the posterior group common electrode of the first transducer assembly unit as well as the anterior group common electrode of the second assembly unit is turned ON, holding the posterior group common electrode of the second assembly unit in OFF state. Further, at the time of putting the transducer elements of the second transducer assembly unit in action, both of anterior and posterior group common electrodes of the second transducer assembly unit are turned ON, while the anterior and posterior group common electrodes of the first transducer assembly unit are held in OFF state.

The separate electrodes which are short circuited to one wiring cable are not necessarily required to be located in the same positions in different transducer assembly units. In short, signal lines of transducer elements which are not interrelated for simultaneous action are short circuited and connected to one wiring cable. The number of transducer assembly units is two or a greater, that is to say, can be three or four. Further, the number of transducer elements which are connected to a common electrode depends on the number of transducer elements which are interrelated for simultaneous action, and cannot be less than the number of transducer elements of simultaneous action by two. Otherwise, for example, equal number of transducer elements can be allotted to the anterior and posterior group common electrodes. In this regard, in a case where a couple of transducer elements are driven simultaneously, an anterior group common electrode in each transducer assembly unit is connected to a single transducer element, and the remainder are connected to a posterior group common electrode. Strictly speaking, the anterior group common electrode which connected to a single transducer element cannot be regarded as "a common electrode" but it functions in the same way as the posterior group common electrode. Therefore, functionally it should be regarded as a common electrode although it is connected to one transducer element only.

The above and other objects, features and advantages of the present invention will become apparent from the following particular description of the invention, taken in conjunction with the accompanying drawings which show by way of example some preferred embodiments of the invention. Needless to say, the present invention should not be construed as being limited to the particular forms shown in the drawings.

DESCRIPTION OF PREFERRED EMBODIMENTS

Figure 1:
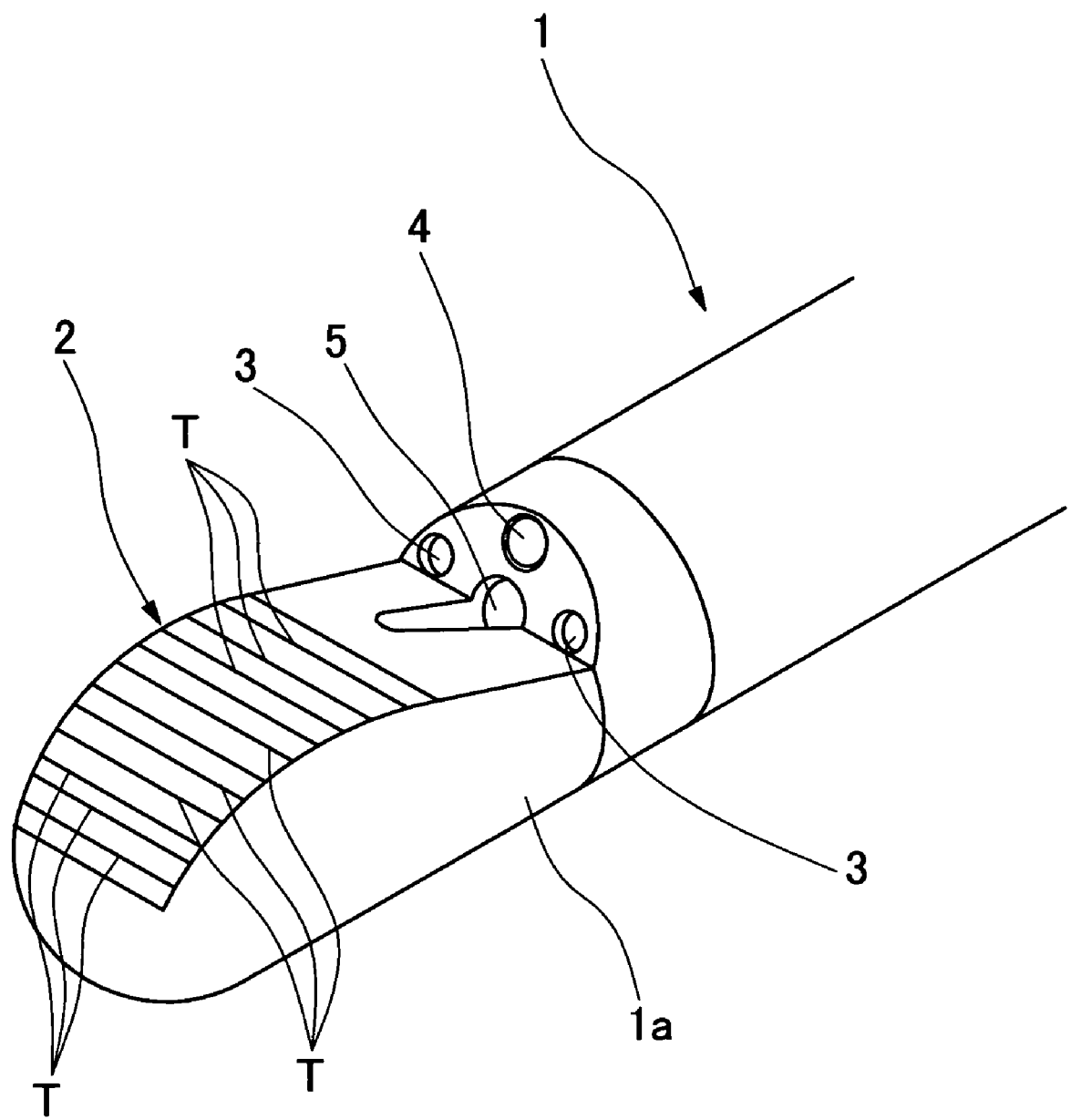
FIG. 1 is a schematic perspective view of an ultrasound diagnostic instrument according to the present invention, which is applied to an ultrasound endoscope and incorporate into a fore end portion of an elongated insertion tube.

Hereafter, the present invention is described more particularly by way of its preferred embodiments, with reference to the accompanying drawings. Referring first to FIG. 1, there is shown a fore end portion of an insertion tube of an ultrasound endoscope embodying the ultrasound diagnostic instrument according to the present invention. Application of the ultrasound diagnostic instrument according to the present invention is not limited to ultrasound probes or endoscopes. Namely, the ultrasound diagnostic instrument of the invention can be applied not only as an insertion type diagnostic instrument which makes intracavitary scans like an endoscope, but also as an external diagnostic instrument which makes scans of internal body tissues through the outer skin of patient.

In FIG. 1, indicated at 1 is an insertion tube to be introduced into a body cavity of a patient. An ultrasound transducer assembly 2 is mounted in a front side of a rigid tip end section 1a of the insertion tube 1. At the proximal end of a down slope behind the ultrasound assembly 2, the rigid tip end section is provided with a semi-circular obliquely reclined wall with illumination windows 3 and an observation window 4 in a proximal end portion which accommodates an endoscopic observation mechanism. Provided between the ultrasound transducer unit 2 of the ultrasound diagnostic instrument and the endoscopic observation mechanism is an outlet opening 5 of a biopsy channel through which a biopsy or surgical instrument is projected into a body cavity under observation.

The ultrasound transducer 2 is constituted by a large number of transducer elements T which are arrayed from a proximal base end portion toward a fore distal end of the rigid tip end section 1a. In the case of the particular example shown, the transducer elements T are arranged in a convexly arcuate shape which is suitable for the so-called convex electronic ultrasound scans. Nevertheless, the ultrasound transducer may have the transducer elements arranged in other directions or in other shapes. For example, the transducer elements may be arrayed in a linear or cylindrical shape or otherwise may be arrayed in X- and Y-directions like a matrix.

Figure 2:
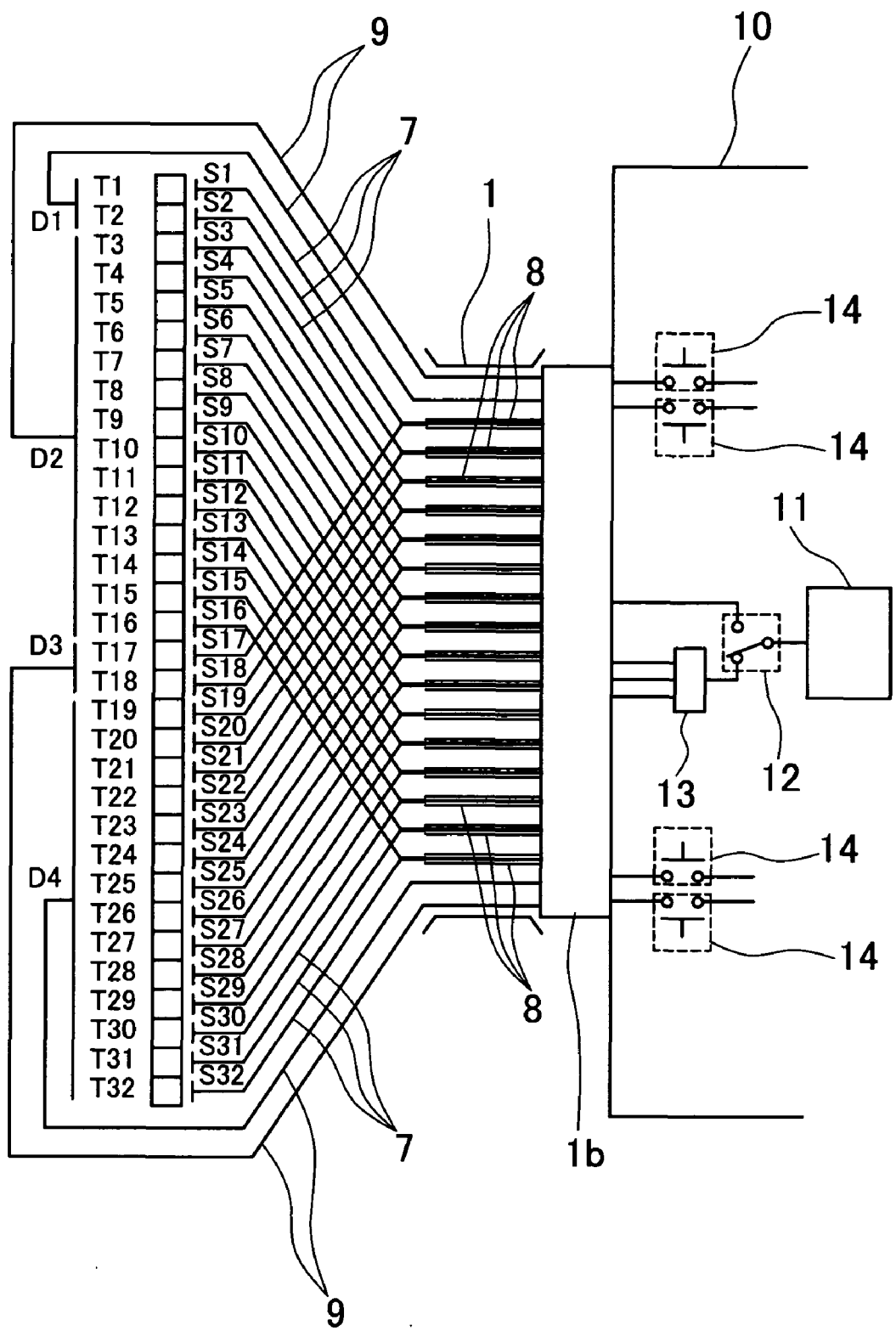
FIG. 2 is a wiring diagram of an ultrasound transducer.

As described hereinbefore, the ultrasound transducer 2 is constituted by an array of a large number of ultrasound transducer elements T. In the case of the particular embodiment shown, the ultrasound transducer 2 is provided with an array of 32 transducer elements as shown in FIG. 2. Generally, an ultrasound transducer element T is provided with an electrode S on one side and an electrode D on the other side. By applying a predetermined voltage to the electrode S while retaining the electrode D at the ground potential, an ultrasound pulse is transmitted into a patient's body to receive echoes from internal body tissues. Accordingly, it is necessary to make a separate wiring connection to the electrode S on each one of the ultrasound transducer elements T in the array, but the electrodes D on the other side of the transducer elements T can be connected to a single wire of a common electrode. The number of ultrasound transducer elements has to be increased as much as possible in order to get a clear ultrasound image of high resolution on a monitor screen.

Wiring hard-wires from the transducer elements T are passed through the insertion tube 1 and extended as far as an ultrasound image observation terminal. Especially, in case the ultrasound diagnostic instrument is applied to an endoscope with a solid-state image sensor in an endoscopic image pickup system, the wiring hard-wires which have to be completely shielded to transmit weak signals of received ultrasound echoes without picking up noises from wiring hard-wires to and from the solid-state image sensor which are also passed through the endoscopic insertion tube 1. Normally, a coaxial cable is used for wiring from each individual electrode S, so that internal space of the insertion tube is mostly occupied by wiring cables from the ultrasound transducer 2.

According to the present invention, while increasing the number of the transducer elements T of the ultrasound transducer 2, attempts have been made to minimize the diameter of the insertion tube 1.

An assembly of 32 transducer elements is employed in the case of the ultrasound transducer 2 exemplified in FIG. 2. The 32 transducer elements T are labeled with reference numerals T1 to T32, while individual electrodes S which are connected to the transducer elements T are labeled with reference numerals S1 to S32, respectively. Of the 32 transducer elements T, transducer elements T1 to T16 are grouped as a first transducer assembly unit, and transducer elements T17 to T32 are grouped as a second transducer assembly unit. With regard to the common electrodes D, the transducer elements T1 and T2 of the first transducer assembly unit are connected an anterior group common electrode D1, while the transducer elements T3 to T16 of the first transducer assembly unit are connected to a posterior group common electrode D2. On the other hand, the transducer elements T17 and T18 of the second transducer assembly unit are connected to an anterior group common electrode D3, and the transducer elements T19 to T20 of the second transducer assembly unit are connected to a posterior group common electrode D4.

Figure 3:
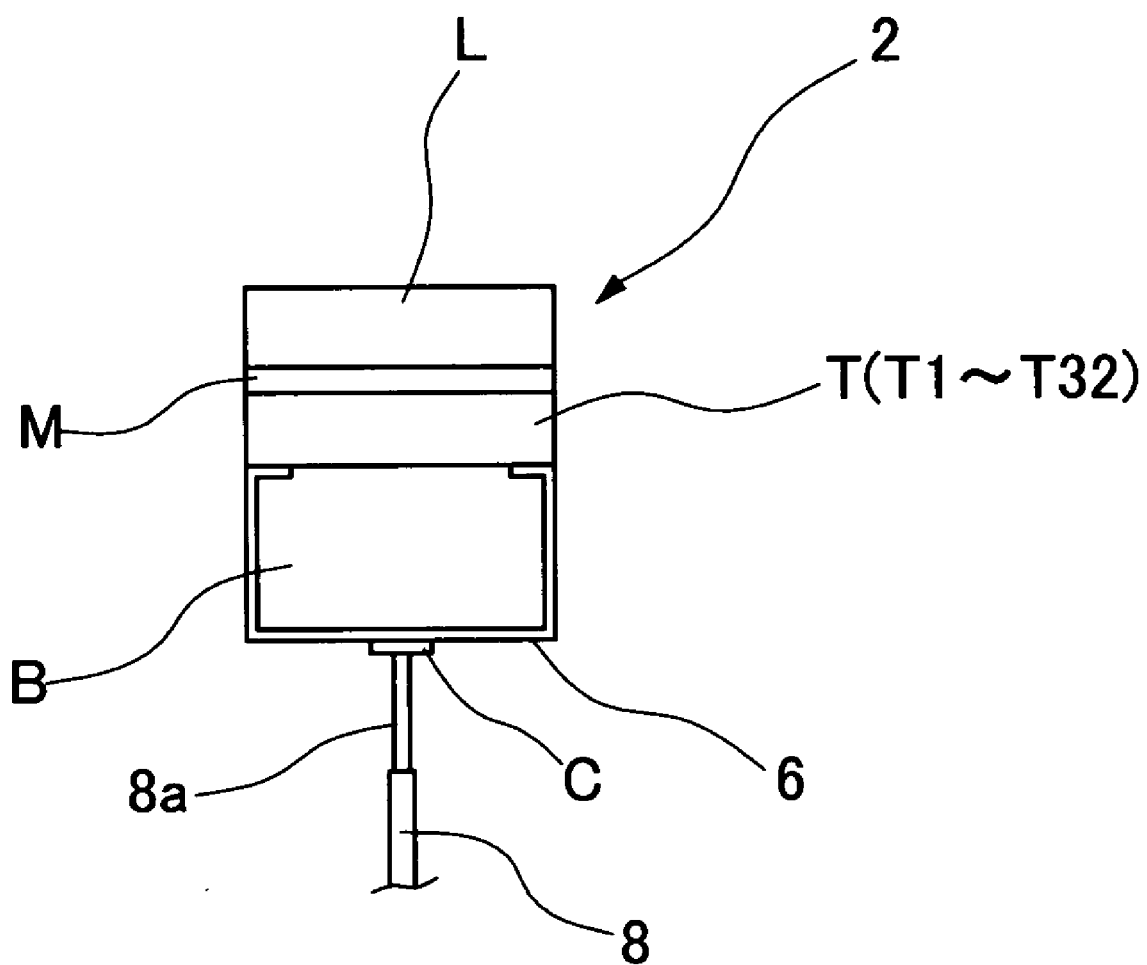
FIG. 3 is a schematic side view of the ultrasound transducer fitted with a filmy wiring board.

Shown in FIG. 3 is the construction of the ultrasound transducer 2. In this case, the 32 transducer elements T of the ultrasound transducer 2 are arrayed in a direction perpendicular to the plane of that figure. The assembly of the transducer elements T is in the form of a multi-layer laminated structure having an acoustic matching layer M and an acoustic lens L laminated on the outer side of the transducer elements T and having a backing material B laminated on the other side. In this instance, the acoustic matching layer M, acoustic lens L and backing material B are provided commonly for each one of the 32 transducer elements T1 to T32.

Figure 4:
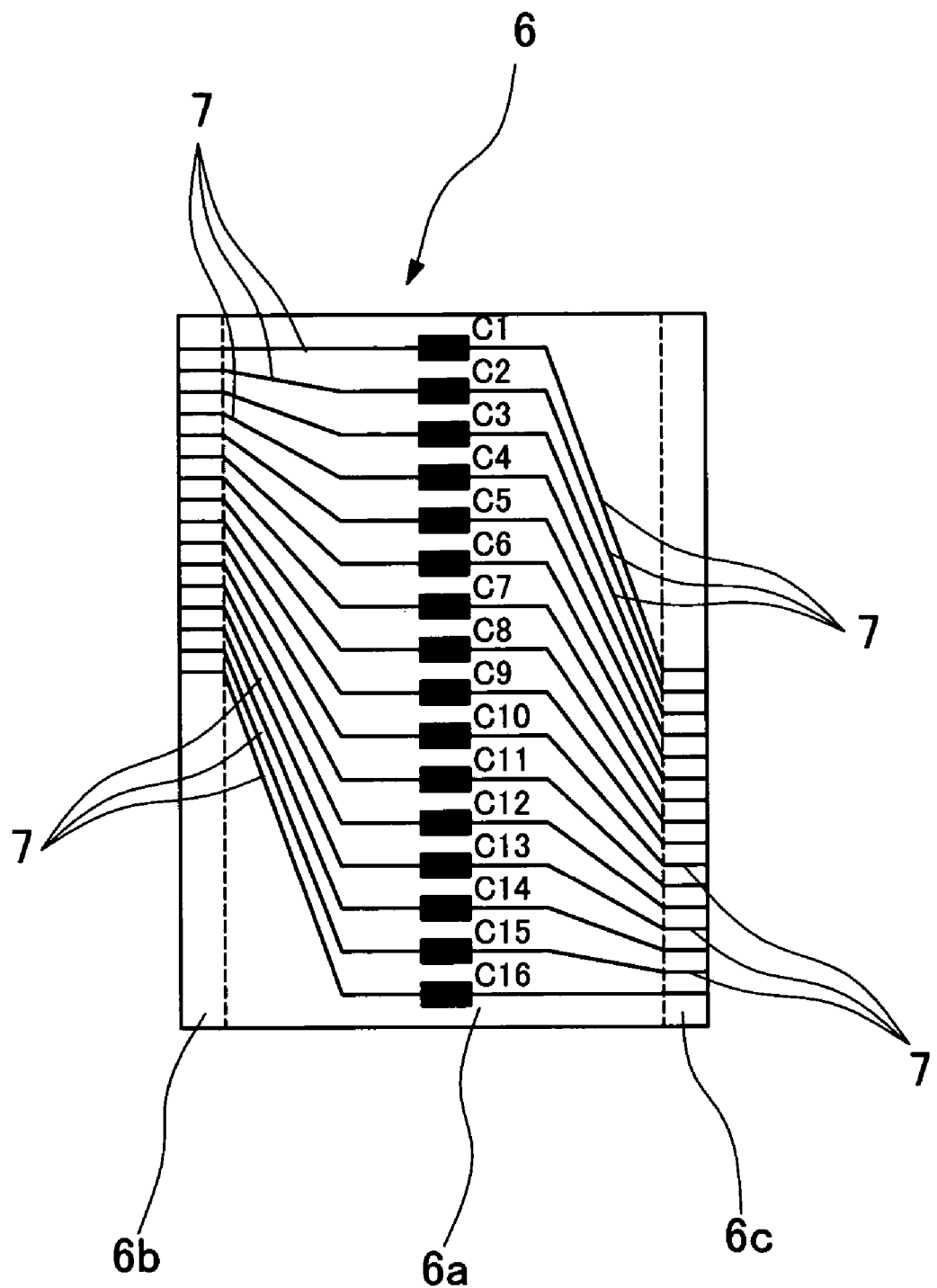
FIG. 4 is a schematic view of the filmy wiring board.

Shown in FIG. 4 is an example of a flexible filmy wiring board 6 to be mounted on the ultrasound transducer 2. As seen in FIG. 4, the filmy wiring board 6 bears a wiring pattern on a flexible synthetic resin sheet. The wiring pattern on the filmy wiring board 6 is formed to make wiring connections to the respective separate electrodes S. More particularly, the wiring pattern contains contact points C1 to C 16 for lines 7 to be connected to separate electrodes S1 and S17, separate electrodes S2, separate electrodes S18, S3 and S19 and so forth. Thus, at the contact points C1 to C16, wiring lines to the separate electrodes S1 to S18 and wiring lines to the separate electrodes S17 to S32 are successively connected in a short-circuited state. A row of contact points C1 to C16 is provided in a center zone 6a of the filmy wiring board 6 which has a predetermined width, between connecting wire portions 6b and 6c running to the opposite side edges of the filmy wiring board 6 for connection to the ultrasound transducer 2. In mounting the filmy wring board 6 on the ultrasound transducer 2, the filmy wiring board 6 is mounted in such a way as to embrace the backing material of the ultrasound transducer 2. Connecting portions 6b at one side of the filmy wiring board 6 are bonded on to make electrical connections to the separate electrodes S1 to S16 of the transducer elements T1 to T16, respectively, while the connecting portions 6c at the other side of the filmy wiring board 6 are similarly bonded on to make electrical connections to the separate electrodes S17 to S32 of the transducer elements T17 to T32, respectively. Further, the center zone 6a of the filmy wiring board 6 is wrapped around the rear and lateral sides of the backing material B, so that the contact points C1 to C16 are located in an exposed state on the lower or back side of the backing material B. Accordingly, as clear from FIG. 3, on the back side of the ultrasound transducer 2, core wires 8a of separate electrode wiring cables 8 are connected to the respective contact points C1 to C16.

The above-described wiring pattern on the filmy wiring board 6 makes it possible to reduce by half the number of wiring cables 8 to the 32 separate electrodes S, that is to say, to reduce the number of wiring cables 8 to 16 which is half the number of connecting conduction lines 7. Each separate electrode wiring cable 8 is connected to a couple of connecting conduction lines 7 which are connected to a pair of separate electrodes S. The separate electrodes S1 to S16 in the first transducer assembly unit are paired with the separate electrodes S17 to S32 in the second transducer assembly unit, respectively. In other words, the separate electrodes in the first transducer assembly unit are paired with the separate electrodes in the corresponding positions in the second transducer assembly unit.

Figure 5:
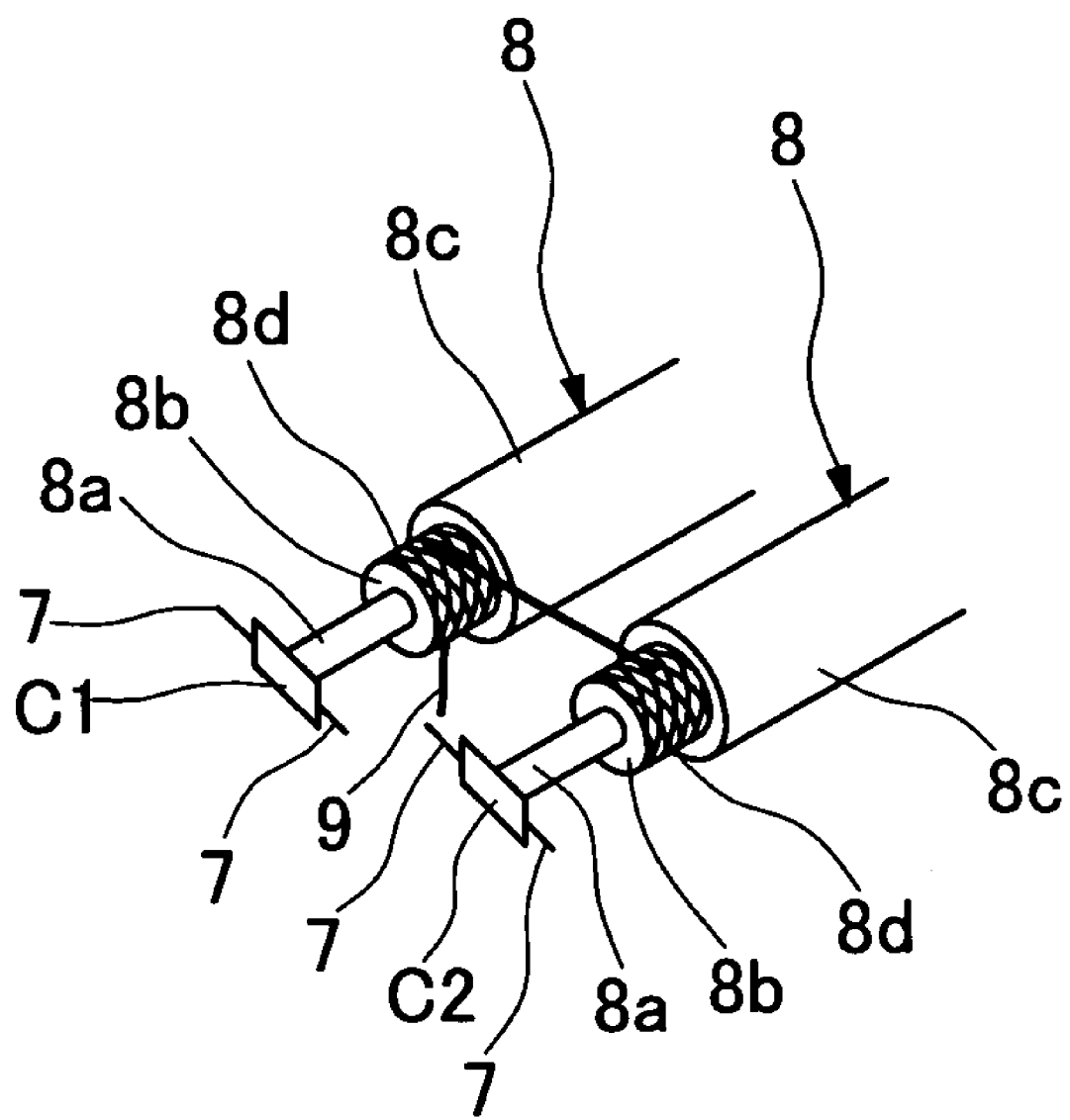
FIG. 5 is a schematic illustration showing the manner of separate electrodes to separate electrode wiring cables.

On the other hand, wiring connections to the common electrodes D1 to D4 may be made by way of the filmy wiring board 6 or otherwise by the use of independent wire cables 9. However, in a case where coaxial cables are used for the separate electrode wiring cables 8 as shown in FIG. 5, a core wire of each coaxial cable is connected to a couple of connecting conduction lines 7, and a braided wire 8d which is provided between an insulating layer 8b and a cover layer 8c can be utilized as a transmission path of the common electrodes D1 to D4. In such a case, the common electrode wiring cables 9 from the common electrodes D1 to D4 may be connected to braided wires on four of the separate electrode wiring cables 8, while dividing the remaining 28 separate electrode wiring cables 8 into four groups and conducting with each other the braid wires 8d on the separate electrode wiring cables 8 of each group. More particularly, in FIG. 2, a braid wire 8d on one of the separate electrode wiring cables 8 in the first and second positions from the top side is connected to the common electrode 8d and at the same time put in conduction with a braid wire 8d on the other separate electrode wiring cable 8. A braid wire 8d on one of the separate electrode wiring cables 8 in the third to eighth positions is connected to the common electrode D2 and at the same time put in conduction with braid wires 8d on other separate electrode wiring cables 8. A braid wire 8d on one of the separate electrode wiring cables 8 in the ninth and tenth positions is connected to the common electrode D3 and at the same time put in conduction with a braid wire 8d on the other separate electrode wiring cable 8. Further, a braid wire 8d on one of the separate electrode wiring cables 8 in the eleventh to sixteenth positions are connected to the common electrode D4 and at the same time put in conduction with braid wires 8d on other separate electrode wiring cables 8.

Further, the above-mentioned sixteen separate electrode wiring cables 8 (plus four common electrode wiring cables 9 in case these independent wiring cable are provided) are led into the insertion tube 1 of the endoscope and encased in a cable (not shown) which is led out of the endoscope and, as shown in FIG. 2, terminated with a connector 1b at an outer distal end to be disconnectibly connected to an ultrasound image observation terminal 10.

Figure 6:
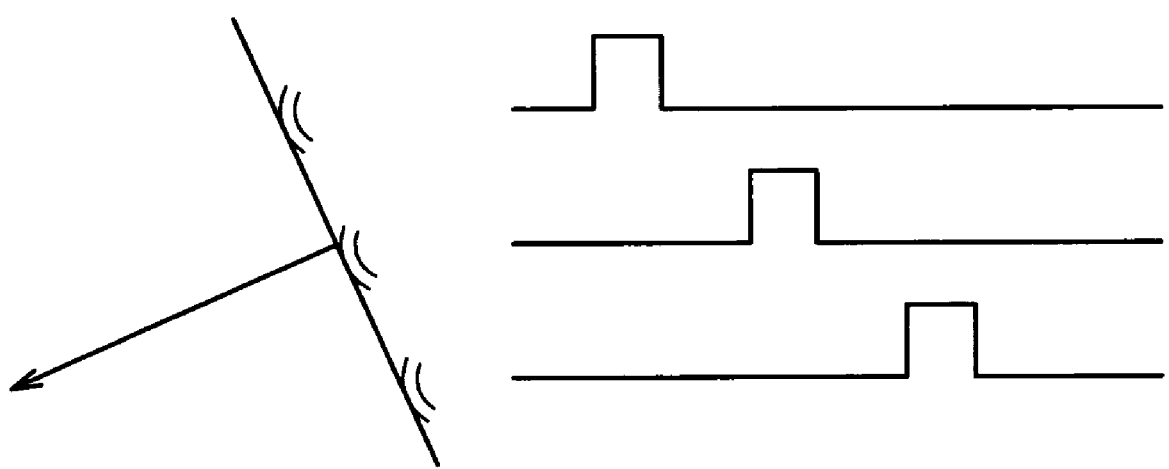
FIG. 6 is a delay timing chart shown as an example of delay control by a delay circuit.

As shown schematically in FIG. 2, the ultrasound image observation terminal 10 is provided with a transmit/reception circuit 11 which is provided with a switch 12 to switch its operation between transmit and reception modes. A delay circuit 13 is connected to the transmit side of the transmit/reception circuit 11. As soon as a drive pulse is fed to the delay circuit 13, three ultrasound transducer elements T are activated by drive pulses in a simultaneous action mode. For example, drive pulses to the three transducer elements T are sequentially delayed as shown in FIG. 6 for the purpose of changing directivity of ultrasound pulses or for controlling a beam pattern. However, if desired, all of the three transducer elements T of the simultaneous action group may be put in transmit action simultaneously, or transmit timing of the transducer elements T in preceding and succeeding positions may be shifted relative to that of the transducer element T in an intermediate position.

On the other hand, a switching element 14 is connected to each one of the wiring cables 9 from the common electrodes D1 to D4. When the switching element 14 is ON and a drive pulse is fed to transducer elements T through a separate electrode wiring cable 8, ultrasound pulses are transmitted from the driven transducer elements T. Namely, as long as the switching element 14 is OFF, no ultrasound pulse is transmitted from transducer elements T even if a drive pulse is supplied thereto.

The ultrasound transducer 2 of the above construction can be used for electronic ultrasound scans in the manner as follows. In making an ultrasound scan, three consecutive transducer elements are driven simultaneously or at least one of three consecutive transducer elements is driven with a delay relative to other transducer elements.

In the first place, among thirty-three transducer elements T, the transducer elements T1 to T3 are driven and put in transmit action. For this purpose, switching elements 14 which are connected to the common electrode wiring cables 9 to the anterior group common electrode D1 and the posterior group common electrode D2 of the first transducer assembly unit are turned ON, while turning OFF the wiring cables 9 to the anterior group common electrode D3 and the posterior group common electrode D4 of the second transducer assembly unit. Then, a drive signal is applied to the transducer elements T1 to T3 from the separate electrodes S1 to S3, respectively. Whereupon, ultrasound is transmitted from the transducer elements T1 to T3. The separate electrode wiring cables 8 which are connected to the separate electrodes S1 to S3 of the transducer elements T1 to T3 are also connected to the separate electrodes S17 to S19 of the second transducer assembly unit. However, since the anterior group common electrode D3 and the posterior group common electrode D4 are OFF, no ultrasound is transmitted from the transducer elements T17 to T19 of the second transducer assembly unit.

Upon completion of ultrasound transmit and reception by the transducer elements T1 to T3, following transducer elements are sequentially driven in the order of transducer elements T2 to T4, transducer elements T3 to T5 and so forth. Upon completion of transmit and reception by the transducer elements T14 to T16, the switching elements 14 of the common electrode wiring cables 9 from the anterior group common electrode D1 of the first transducer assembly unit are turned OFF, while holding ON the switching elements 14 of the common electrode wiring cables 9 from the posterior group common electrode D2, with the anterior and posterior group common electrodes D3 and D4 of the second transducer assembly unit in ON and OFF states, respectively. In this state, a drive signal is applied to the separate electrodes S115 and S117 to drive the transducer elements T15 to T17. Namely, in a transitional phase from the first transducer assembly unit to the second transducer assembly unit, the posterior group common electrode D2 of the first transducer assembly unit and the anterior group common electrode D3 of the second transducer assembly unit are held in ON state. Accordingly, the separate electrode S15 is short circuited to the separate electrode S31, the separate electrode S16 is short circuited to the separate electrode S32, and the separate electrode S17 is short circuited to the separate electrode S1. However, since the common electrodes D1 and D2 which are connected with the transducer elements T1, T31 and T32 are in OFF state, no ultrasound is transmitted from these transducer elements T1, T31 and T32. The transducer elements T16 to T18 are driven under similar circumstances. At the time of driving the transducer elements T16 to T18 of the second transducer assembly unit, switching elements 14 of common electrode wiring cables 9 from the anterior and posterior group common electrodes D3 and D4 of the second transducer assembly unit are held in ON state, while the anterior and posterior group common electrodes D1 and D2 of the first transducer assembly unit are held in OFF state. Transducer elements other than T16 to T18 are not driven at this time.

Even though the ultrasound transducer 2 is constituted by thirty-two ultrasound transducer elements T as described above, the insertion tube 1 of the endoscope can be made narrower because the number of separate electrode wiring cables 8 to be fitted in the insertion tube 1 of the endoscope can be reduced by half, that is, can be reduced to sixteen cables. Besides, the common electrode is divided into four parts, so that the number of common electrode wiring cables 9 is increased by three as compared with the arrangement in the conventional counterpart. Nevertheless, the total number of cables to be fitted internally of the insertion tube 1 can be reduced drastically. In addition, in a case where the braid wires 8d in the separate electrode wiring cables 8 are used for making wiring connections to the common electrodes D, it suffices to provide only sixteen wiring cables within the insertion tube 1. Such sixteen wiring cables can be bundled into a single slim cord and passed through the insertion tube 1 in a shielded state.

Figure 7:
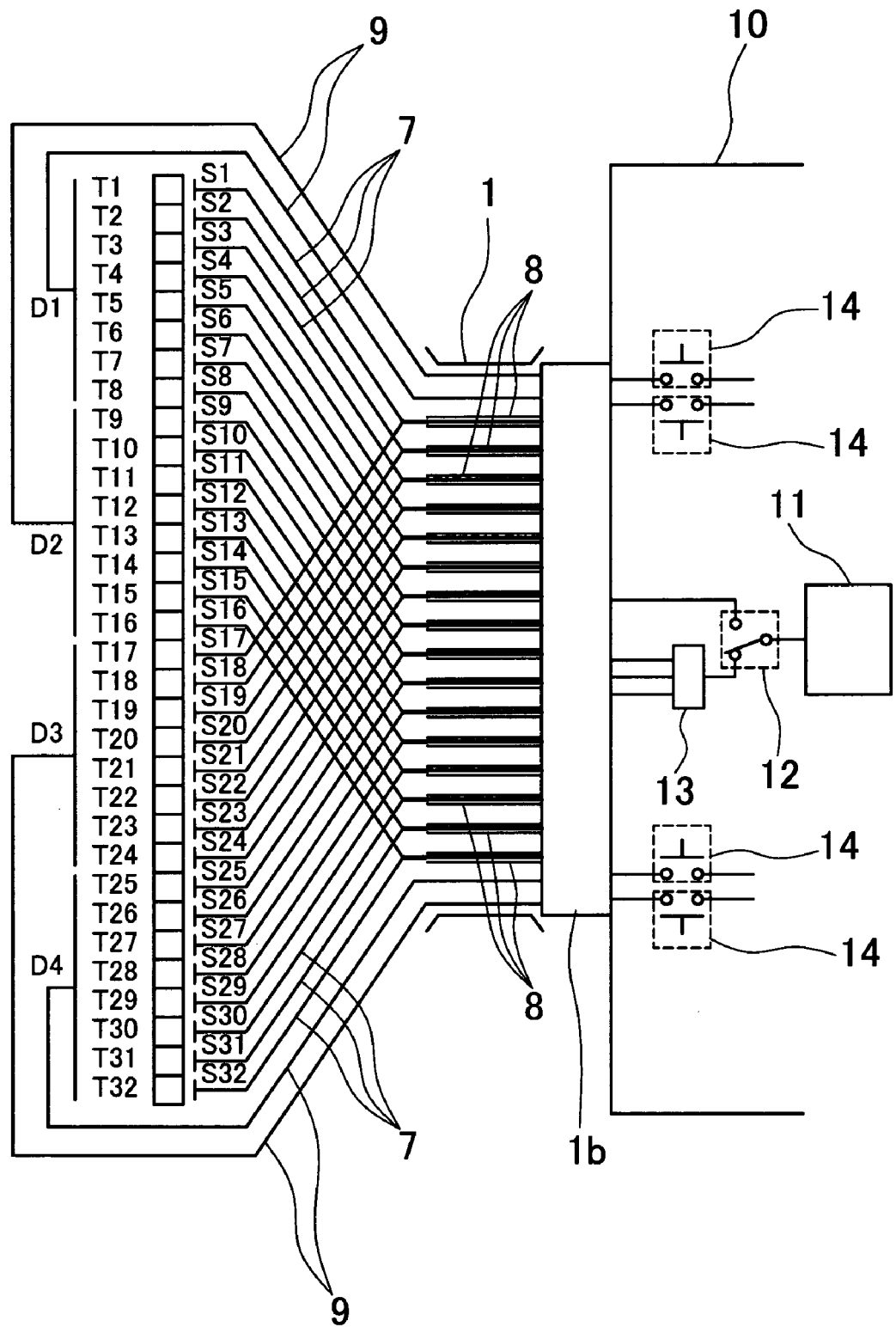
FIG. 7 is a wiring diagram of an ultrasound transducer in a second embodiment of the present invention.

In the above-described ultrasound transducer construction, the transducer is arranged to put three consecutive transducer elements simultaneously in action. If desired, it can be arranged to activate two transducer elements simultaneously. In such a case, the anterior group common electrode in the first and second transducer assembly units can be constituted by a single ultrasound transducer element. In this manner, the anterior and posterior group common electrodes for a plural number of transducer elements in each transducer assembly unit need to be connected to a number of transducer elements which is greater than a number of transducer elements in simultaneous action minus one. That is, in a case where five transducer elements are simultaneously put in action, the common electrode is connected to more than four transducer elements. Accordingly, in a case where, among the sixteen transducer elements in each one of the first and second transducer assembly units, eight transducer elements are connected to each one of the anterior and posterior group common electrodes as shown in FIG. 7, it is possible to drive the respective transducer elements sequentially one after another or to drive simultaneously a desired number of transducer elements at one time. If necessary, three or more transducer assembly units may be incorporated into the ultrasound transducer 2. In this case, a separate electrode wiring cable 8 is connected to a number of separate electrodes corresponding to the number the transducer assembly units.

Figure 8:
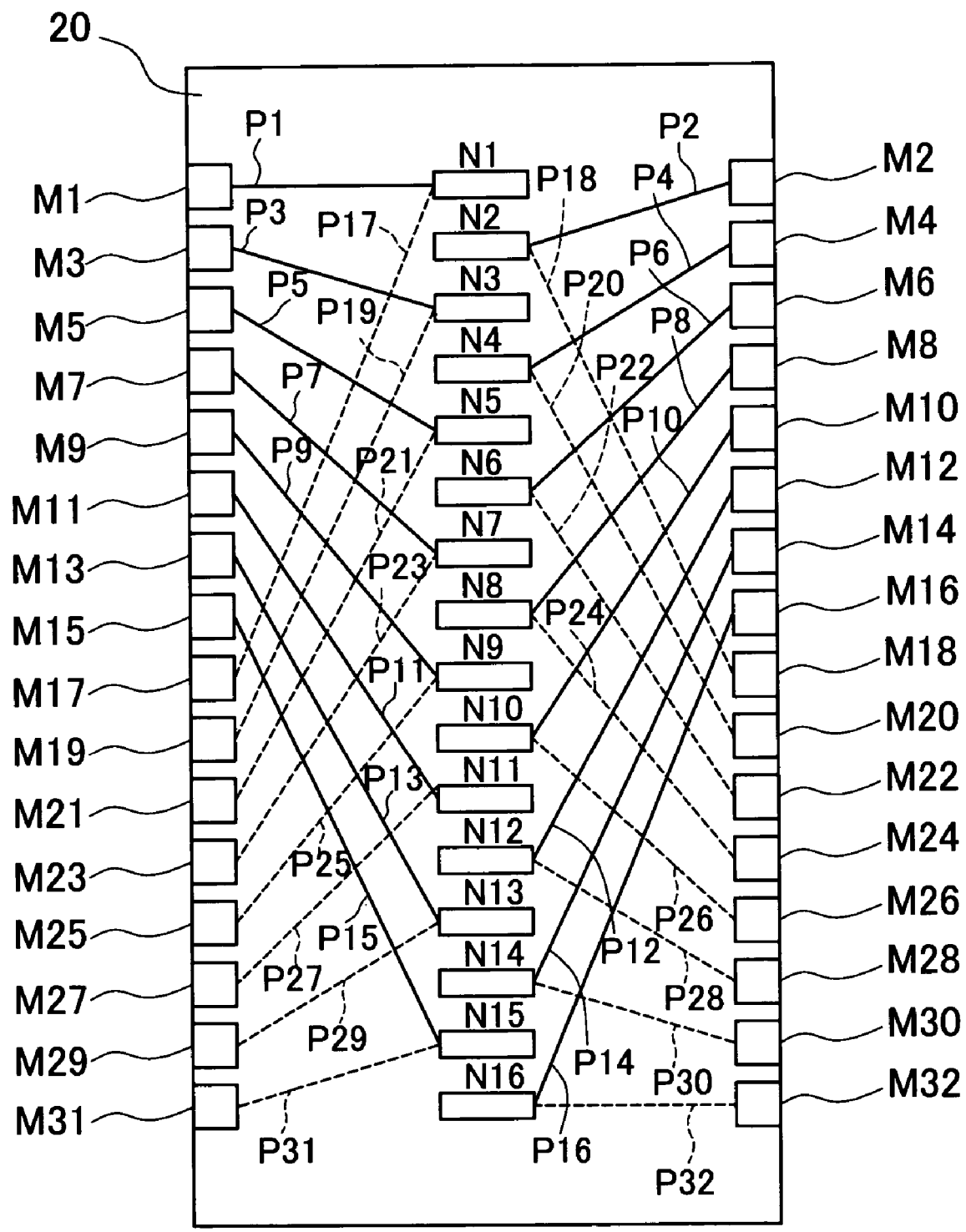
FIG. 8 is a schematic view of a filmy wiring board bearing wiring patterns on its front and rear sides.

Now, referring to FIG. 8, there is shown another embodiment of the present invention. In this embodiment, the conduction lines 7 are provided as a printed pattern on a filmy wiring board, and separate electrode wiring cables 8 are directly connected to the ultrasound transducer 2. Therefore, contact points M for connection to the respective separate electrodes S of the transducer elements T are provided on the filmy wiring board 20, along with contact points N for connection to the respective separate electrode wiring cables 8 and a printed wiring pattern P connecting the contact point M to the contact points N. In this instance, the contact points, M1 to M32, on the side of the transducer elements T are provided in the same number as the separate electrodes S of the transducer elements T. The number of the contact points, N1 to N16, on the side of the separate electrode wiring cables 8 is half the number of the contact points M. The wiring pattern P is constituted by wiring lines P1 to P32, the same number as the contact points M on the side of the transducer elements T.

Conduction lines 7 are connected in pairs to each one of the separate electrode wiring cable 8, so that they are crossed at least at some points. Therefore, both sides of the filmy wiring board 20 are used for routing the wiring pattern P. Besides, the contact points N for the separate electrode wiring cables are located at transversely intermediate positions on the filmy wiring board 20, between the contact points M which are located at intervals along opposite side edges of the filmy wiring board 20. Accordingly, the contact points M and N are arranged in three rows running longitudinally along the opposite side edges and a center line of the filmy wiring board 20 and each containing the same number of contact points, that is to say, each containing eight contact points.

The ultrasound transducer elements T are each in the form of a short strip of a predetermined length. Of the transducer elements T1 to T32 in a linear array, those transducer elements which are in odd-number positions have a separate electrode located in the vicinity of a left end of a strip-like body, while those transducer elements which are in even-number positions have a separate electrode located in the vicinity of a right end of the strip-like body. That is to say, the separate electrodes are located alternately at a left end and at a right end of the arrayed transducer elements T. The wiring pattern lines P1 to P16 which are connected to the separate electrode S1 to S16 of the transducer elements T1 to T16 are formed on the front side of the filmy wiring board 20 (the side on which the contact points M and N are provided), while the wiring pattern lines P17 to P32 which are connected to the separate electrodes S17 to S32 of the transducer elements T17 to T32 are formed on the opposite rear side of the filmy wiring board 20 (on the side away from the side with the contact points M and N). Therefore, all of the wiring pattern lines can be formed on the filmy wiring board 20 without crossing each other.

Since the wiring pattern P is formed partly on the front side and partly on the rear side of the filmy wiring board 20 in the manner as described above, the contact points M on the side of the transducer elements T as well as the contact points N on the side of the separate electrode wiring cables are all exposed on both sides of the filmy wiring board 20. Therefore, for example, the respective contact points M and N which are electrically connected with the wiring pattern lines P on the front and rear sides of the filmy wiring board 20 can be formed by filling conductive material in apertures which are perforated in the filmy wiring board 20 in relation with positions of the wiring pattern lines P.

Thus, in connecting the separate electrode wiring cables 8 with the separate electrodes S of the transducer elements T by way of the filmy wiring board 20 and in short circuiting a couple of separate electrodes by a separate electrode wiring cable 8 in the manner as described above, the wiring pattern lines P are not crossed at any point. In addition, since the contact points M on the side of the transducer elements are alternately allotted to the opposite side edges of the filmy wiring board 20, each contact point M can be formed on a relative wide area for facilitating registration of position of the filmy wiring board 20 on the ultrasound transducer 20, permitting to assemble a wiring board of the separate electrode wiring cables into the ultrasound transducer 2 with accuracy.

Figure 9:
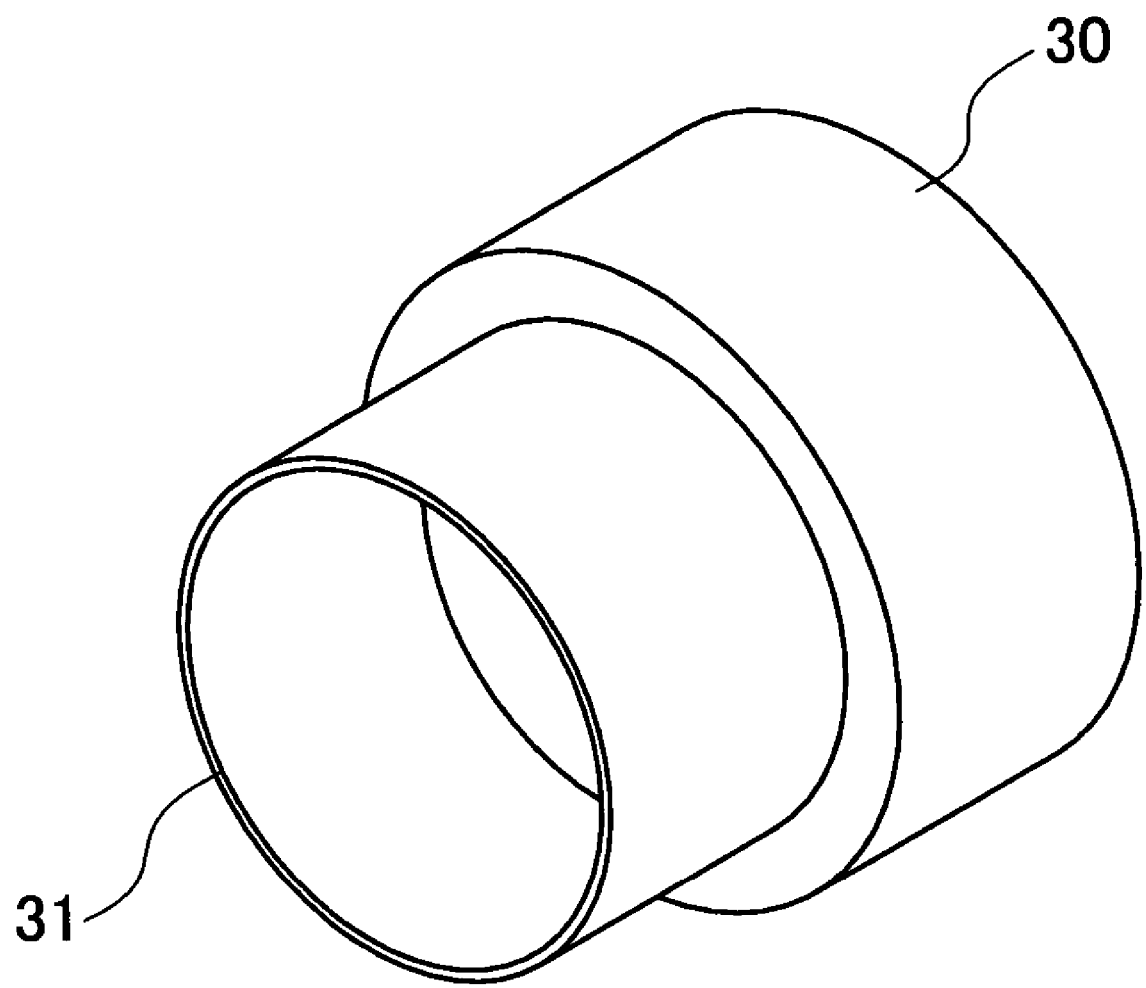
FIG. 9 is a schematic perspective view of an radial array ultrasound transducer.
Figure 10:
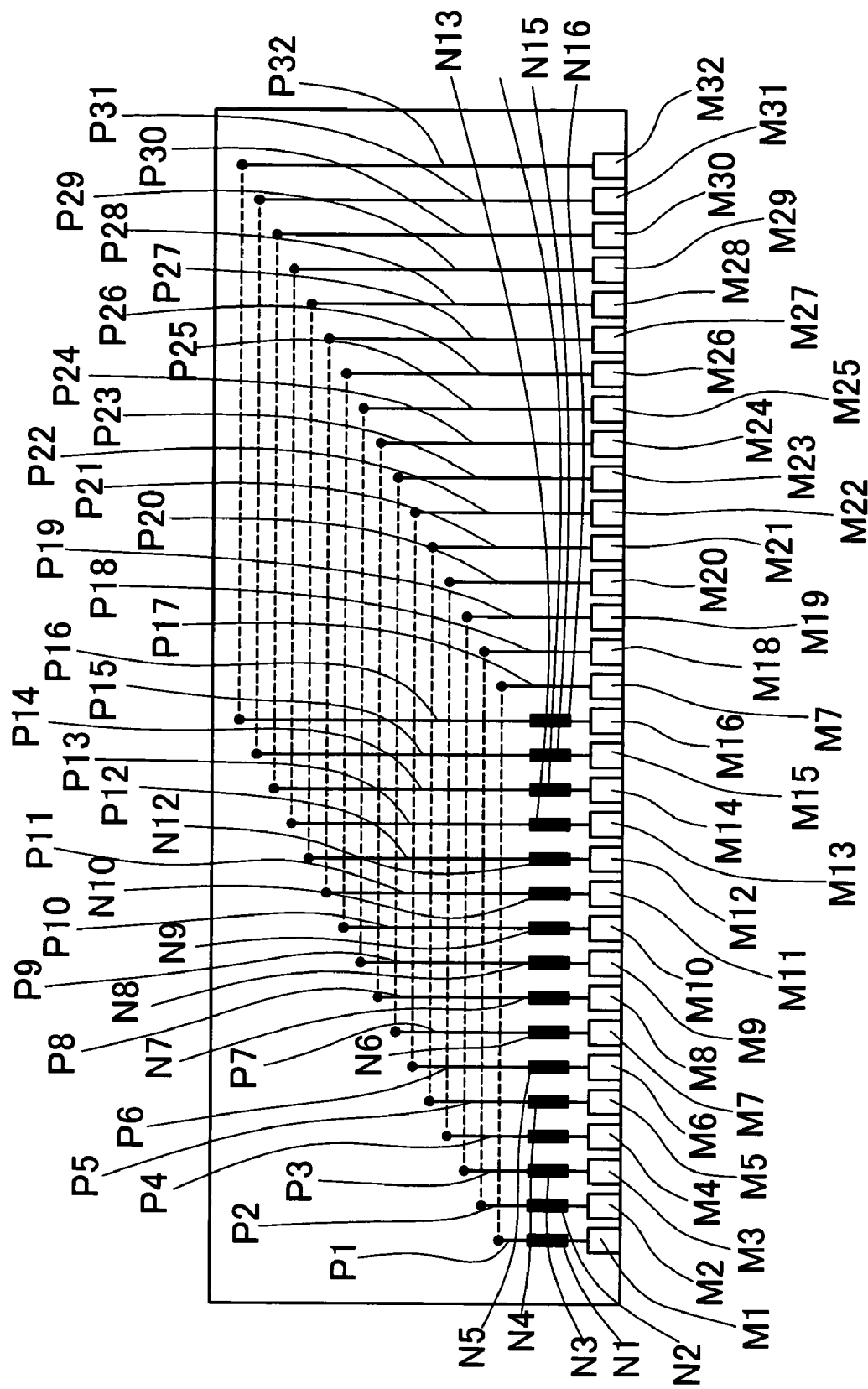
FIG. 10 is diagrammatic view of a filmy wiring board for use on the ultrasound transducer of FIG. 9.

Further, for example, the present invention can be applied to an ultrasound transducer 30 having a large number of transducer elements T arranged in a cylindrical array as shown in FIG. 9. In this case, a cylindrical filmy wiring board 31 is used for the cylindrical transducer array. As shown in FIG. 10, contact points M on the side of transducer elements and contact points N on the side separate electrode wiring cables are likewise connected with wiring pattern lines P on the front and rear sides of the filmy wiring board 31.

In this instance, the transducer elements T are divided into two groups. Namely, the transducer elements are divided into Group I consisting of transducer elements T1 to T16 and Group II consisting of transducer elements T17 to T32. As shown in FIG. 10, the filmy wiring board 31 is provided with contact points M1 to M16 on its front side for connection to separate electrodes S1 to S16 of the transducer elements T1 to T16, along with contact points M17 to M32 to be connected to separate electrodes S17 to S32 of the transducer elements T17 to T32. Contact points N1 to N16 for the separate electrode wiring cables are connected to wiring pattern lines P1 to P16, respectively. Wiring pattern lines P1 to P16 as well as wiring pattern lines P17 to P32 are connected to conduction points (indicated by a black dot in FIG. 10) which are formed through the filmy wiring board 31. Further, the wiring pattern lines P1 to P16 are short circuited with a corresponding one of the wiring pattern lines P17 to P32 by a wiring pattern (indicated by broken lines) which is formed on the rear side of the filmy wiring board 31. By the use of the filmy wiring board 31, it becomes possible to reduce by half the number of the separate electrode wiring cables as compared with the number of the transducer elements on the ultrasound transducer 30. This ultrasound transducer 30 operates in the same manner as in the foregoing embodiments.

What is claimed is:

1. An electronic scan type ultrasound diagnostic instrument comprising:
    an ultrasound transducer including a linearly or arcuately arranged array of transducer elements, and adapted to make an electronic scan by sequentially driving a plural number of adjacently located transducer elements into interrelated simultaneous or delayed actions, wherein:
    said transducer elements are divided into a plural number of transducer assembly units in the direction of said transducer array;
    each one of said transducer elements is provided with a separate electrode connected with an ultrasound signal transmit/reception line separately from other transducer elements and a common electrode connected with a common electrode of one or a plural number of other transducer elements;
    further comprising a filmy wiring board arranged in three rows of a same number of contact points running longitudinally along opposite side edges to be connected to respective separate electrodes of said transducer elements and along a center line thereof to be connected with separate electrode wiring cables,
    wherein said filmy wiring board includes a wiring pattern on front and rear sides thereof, said wiring pattern on the rear side being led out onto the front side by conductive parts inlayed through said filmy wiring board; and
    said wiring pattern including a number of signal lines separately connected to said separate electrodes, each one of said signal lines being short circuited with a signal line from a transducer element in a corresponding position in another transducer assembly unit and connected together to one same wiring cable.

2. An electronic scan type ultrasound diagnostic instrument as defined in claim 1, wherein said ultrasound transducer is provided as an ultrasound scan head at the fore end of an insertion tube of an endoscope.

3. An electronic scan type ultrasound diagnostic instrument as defined in claim 2, wherein said endoscope is further provided with an optical observation means immediately behind said ultrasound scan head.

4. An electronic scan type ultrasound diagnostic instrument as defined in claim 1, wherein common electrodes of ultrasound elements in each transducer assembly unit are divided into an anterior group and a posterior group, and an independent switching means is connected to a wiring cable to each group of common electrodes.

5. An electronic scan type ultrasound diagnostic instrument as defined in claim 4, wherein said anterior group is constituted by a number of common electrodes, which is greater than a number of transducer elements interrelated for simultaneous or delayed actions minus one.

6. An electronic scan type ultrasound diagnostic instrument as defined in claim 4, wherein said anterior and posterior groups are constituted by the same number common electrodes.

7. An electronic scan type ultrasound diagnostic instrument as defined in claim 1, wherein each one of said wiring cables is constituted by a coaxial cable having a core wire connected to separate electrodes of transducer elements, and said common electrodes are connected to a braid wire on one wiring cable which is connected with a braid wire on another wiring cable which braid wire is connected with a common electrode or electrodes of the same group.

8. An electronic scan type ultrasound diagnostic instrument as defined in claim 1, wherein said ultrasound transducer has said transducer elements along a backing material, and said filmy wiring board is wrapped around said backing material with opposite ends thereof tucked in and gripped between said backing material and arrayed transducer elements, and said arrayed transducer elements are connected to said contact points of the opposite side edges alternately in order.

9. An electronic scan type ultrasound diagnostic instrument comprising:

an ultrasound transducer of an array of transducer elements arranged as an annular array in a circumferential direction of an ultrasound scan head, and adapted to make an electronic scan by sequentially driving a plural number of adjacently located transducer elements into interrelated simultaneous or delayed actions, wherein:

said transducer elements are divided into a plural number of transducer assembly units in the direction of said transducer array;

each one of said transducer elements is provided with a separate electrode connected with an ultrasound signal transmit/reception line separately from other transducer elements and a common electrode connected with a common electrode of one or a plural number of other transducer elements;

further comprising signal lines separately connected to separate electrodes of the respective transducer elements, each one of said signal lines being short circuited with a signal line from a transducer element in a corresponding position in another transducer assembly unit and connected together to one and same wiring cable;

said common electrodes being divided into an anterior group and a posterior group in each transducer assembly unit, wiring cables from anterior and posterior group common electrodes in each transducer unit being each connected with an independent switching means, and further comprising a cylindrical filmy wiring board having contact points arranged along one side thereof to be connected respectively to separate electrodes of said transducer elements and wiring lines from said contact points to connect said separate electrodes with said wiring cables in such a way as to short circuit signal lines of said separate electrode, of different groups, wherein said filmy wiring board includes said wiring pattern on front and rear sides thereof, a wiring pattern on the rear side being led out onto the front side by conductive parts inlayed through said filmy wiring board.

* * * * *